United States Patent
Cheng et al.

(10) Patent No.: US 8,979,780 B2
(45) Date of Patent: Mar. 17, 2015

(54) ADJUSTABLE IMMOBILIZING JOINT BRACE

(75) Inventors: Gene C. Cheng, Peoria, IL (US); Arnold R. Ness, Edwards, IL (US)

(73) Assignee: Gene C. Cheng, Peoria, IL (US)

( * ) Notice: Subject to any disclaimer, the term of this patent is extended or adjusted under 35 U.S.C. 154(b) by 738 days.

(21) Appl. No.: 12/066,424

(22) PCT Filed: Mar. 6, 2008

(86) PCT No.: PCT/US2008/056028
§ 371 (c)(1),
(2), (4) Date: Mar. 11, 2008

(87) PCT Pub. No.: WO2009/035717
PCT Pub. Date: Mar. 19, 2009

(65) Prior Publication Data
US 2010/0081978 A1  Apr. 1, 2010

Related U.S. Application Data

(60) Provisional application No. 60/972,598, filed on Sep. 14, 2007.

(51) Int. Cl.
*A61F 5/00* (2006.01)
*A61F 5/37* (2006.01)
*A61F 5/058* (2006.01)

(52) U.S. Cl.
CPC .............................. *A61F 5/05841* (2013.01)
USPC .................. 602/16; 602/20; 602/23; 602/26; 128/878; 128/882

(58) Field of Classification Search
USPC .................. 602/16, 20, 23, 26; 128/878, 882
See application file for complete search history.

(56) References Cited

U.S. PATENT DOCUMENTS

| | | | |
|---|---|---|---|
| 4,953,543 A * | 9/1990 | Grim et al. ...................... 602/16 |
| 5,000,169 A | 3/1991 | Swicegood et al. |
| 5,195,944 A | 3/1993 | Schlogel |
| 5,232,435 A | 8/1993 | Leibinsohn |
| 2,339,515 A | 1/1994 | Parcher |
| 5,437,619 A | 8/1995 | Malewicz et al. |
| 6,080,122 A | 6/2000 | Gulledge |
| 6,375,632 B1 * | 4/2002 | Albrecht et al. ................ 602/16 |
| 6,533,741 B1 | 3/2003 | Lee et al. |

(Continued)

OTHER PUBLICATIONS

International Search Report/Written Opinion for Application No. PCT/US2008/056028 dated Jul. 28, 2008.

(Continued)

*Primary Examiner* — Victoria J Hicks
(74) *Attorney, Agent, or Firm* — Alston & Bird LLP

(57) ABSTRACT

An adjustable immobilizing joint brace has a pair of opposed, spaced apart first supports for supporting and immobilizing a joint. Each first support has a pair of first joint holes proximate a first end. One of the holes of the pair of first joint holes is spaced further from the first end of the first support than the other hole. A pair of opposed, spaced apart second supports has two opposed sides. Each second support has a pair of second joint holes proximate a joint end. The pair of second joint holes can be aligned with and attached to the pair of first joint holes on either side of the first support to form different angles of attachment between the first supports and the second supports depending on the orientation of the first supports relative to the orientation of the second supports.

18 Claims, 4 Drawing Sheets

(56) References Cited

U.S. PATENT DOCUMENTS

| | | |
|---|---|---|
| 6,866,646 B2 | 3/2005 | Hopkins et al. |
| 7,001,349 B2 | 2/2006 | Vollbrecht et al. |
| 2004/0153016 A1 | 8/2004 | Salmon et al. |
| 2006/0247565 A1 | 11/2006 | Cormier et al. |

OTHER PUBLICATIONS

Office Action for Taiwanese Application No. 097129742 dated Jan. 28, 2014.

* cited by examiner

ADJUSTABLE IMMOBILIZING JOINT BRACE

CROSS-REFERENCE TO RELATED APPLICATIONS

This application is a national phase entry of PCT application No. PCT/US08/56028, filed Mar. 6, 2008, entitled "Adjustable Immobilizing Joint Brace," which claims the benefit of U.S. Provisional Patent Application No. 60/972,598 filed on Sep. 14, 2007. These applications are incorporated by reference herein in their entirety.

BACKGROUND OF THE INVENTION

The present invention relates to an adjustable immobilizing joint brace, specifically an immobilizing joint brace that includes a plurality of immobilizing positions.

Following injury and or surgery to a joint such as the elbow or knee, it is often necessary to immobilize the joint while the joint heals. Braces or splints for immobilizing the joint are well known. Many types of braces are available for the knee and elbow that help to keep the joint in a fixed or recovery position. Because the fixed position may vary depending on the injury or individual and it is desirable to vary the angle during recovery, it is often desirable that the immobilizing joint brace be adjustable such that the individual or medical professional can set the joint angle or change the joint angle as healing progresses. However, adjustable braces require additional components such as locking mechanisms which may become loose, lost or corroded. Additionally, adjustable braces often weigh more, cost significantly more and have a larger profile than nonadjustable braces.

What is needed therefore, but not provided in the prior art, is an immobilizing joint brace that can be set to a plurality of various rigid angles while keeping the light weight, low profile and nearly as few components of a non-adjustable brace.

BRIEF SUMMARY OF THE INVENTION

Briefly stated, the present invention is directed to an adjustable immobilizing joint brace that has a pair of opposed, spaced apart first supports. Each first support has a pair of first joint holes proximate a first end. One of the first joint holes is spaced further from the first end of the first support than the other first joint hole. A pair of opposed, spaced apart second supports has two opposed sides. Each second support has a pair of second joint holes proximate a joint end. The second joint holes are aligned with and attached to the first joint holes on either side of the first support such that the first supports are attached to the second supports and form a variable angle which depends on the orientation of the first supports relative to the orientation of the second supports.

In another aspect, the invention is directed to an adjustable immobilizing joint brace that has a generally rigid first support with a first side and a second side and an end that is removably attached to a generally rigid second support that has a first side for attaching to and immobilizing a joint. The first side of the end of the first support is removably mountable to the first side of the end of the second support to form a first angle between the first support and the second support in a first immobilized position. The second side of the end of the first support is removably mountable to the first side of the end of the second support to form a second angle between the first support and the second support in a second immobilized position.

In another aspect, the invention is directed to an adjustable immobilizing joint brace that includes a first support that has a pair of first joint holes proximate a first end. One of the first joint holes is spaced further from the first end of the first support than the other first joint hole. A second support has two opposed sides and a pair of second joint holes proximate a joint end. The second joint holes are aligned with and attached to the first joint holes on either side of the first support such that the first support is attached to the second support and forms a variable angle which depends on the orientation of the first support relative to the orientation of the second support.

BRIEF DESCRIPTION OF THE SEVERAL VIEWS OF THE DRAWINGS

The foregoing summary, as well as the following detailed description of embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
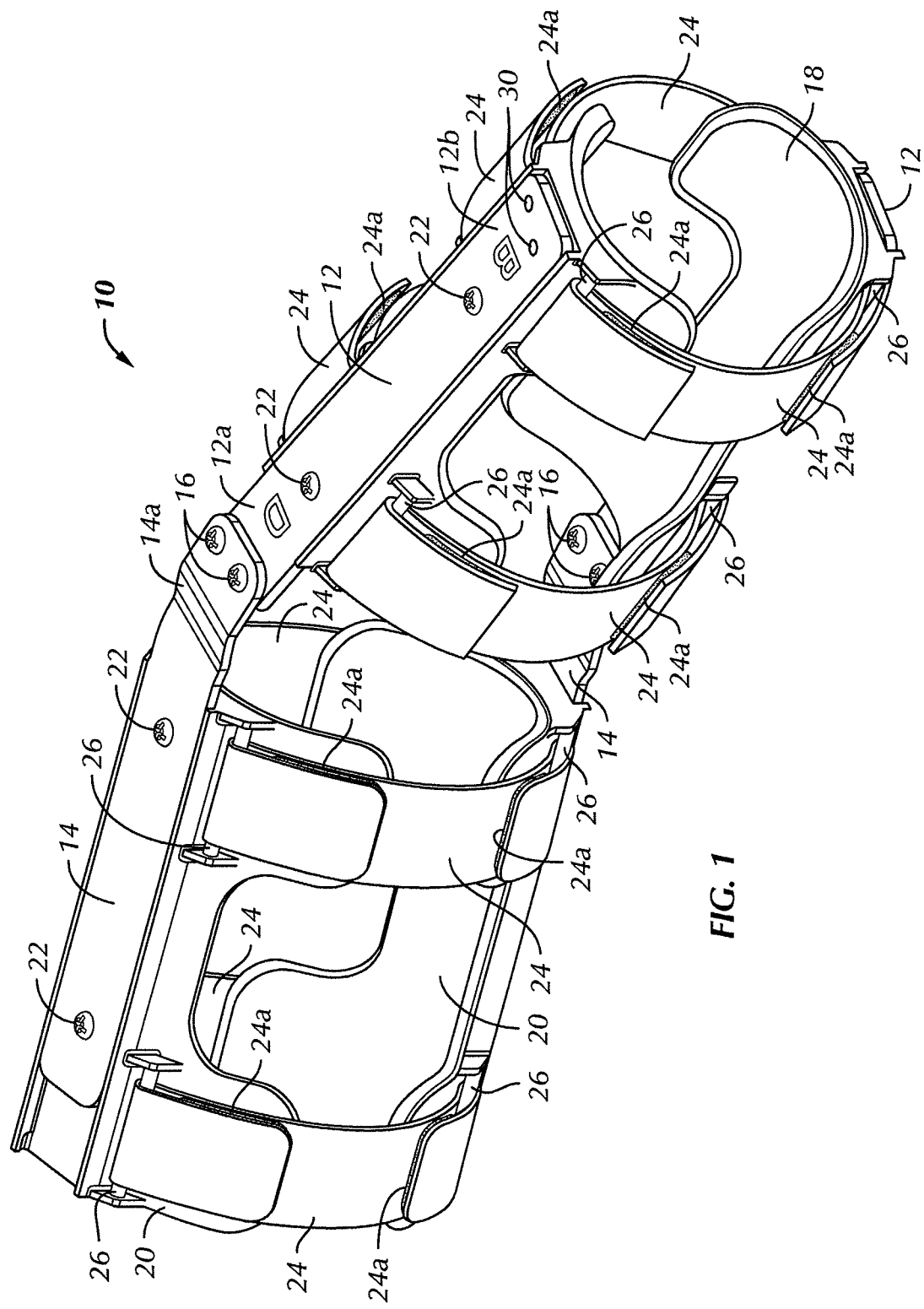
FIG. 1 is a perspective view of the adjustable immobilizing joint brace in accordance with an embodiment of the present invention.
Figure 2:
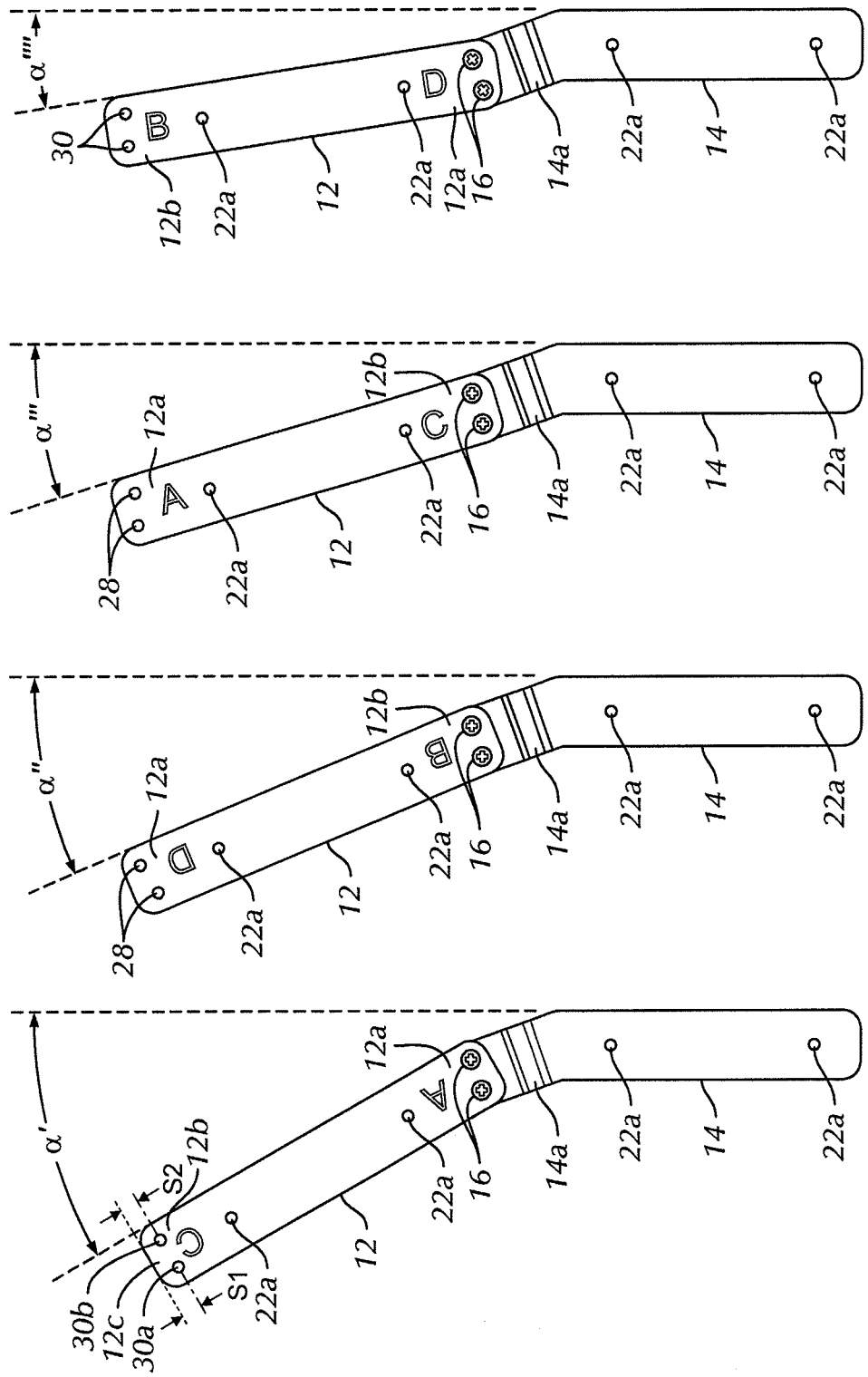
FIG. 2A is a top plan view of assembled first and second supports of the immobilizing joint brace shown in FIG. 1 arranged in a first position.
FIG. 2B is a top plan view of the assembled first and second supports shown in FIG. 2A arranged in a second position.
FIG. 2C is a top plan view of the assembled first and second supports shown in FIG. 2A arranged in a third position.
FIG. 2D is a top plan view of the assembled first and second supports shown in FIG. 2A arranged in a forth position.
Figure 3:
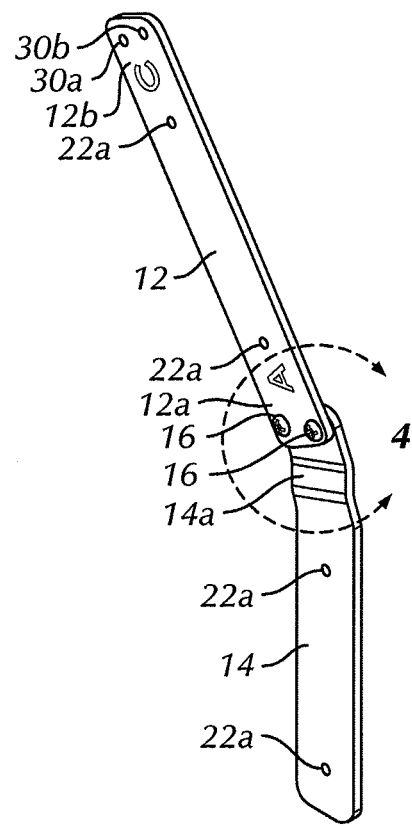
FIG. 3 is a perspective view of the assembled supports shown in FIG. 2A.
Figure 4:
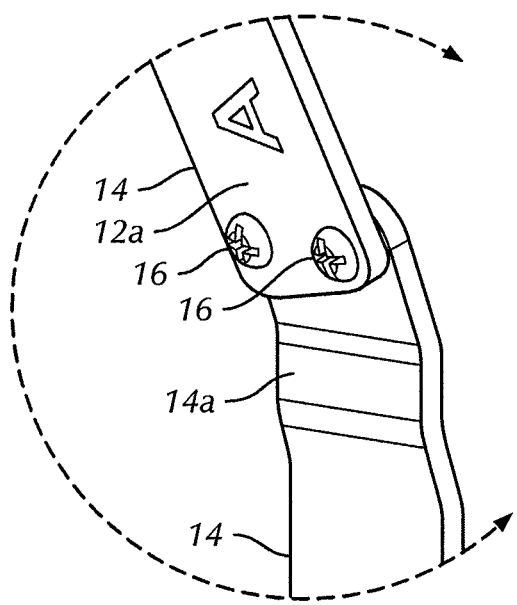
FIG. 4 is an enlarged perspective view of the joint between the assembled supports within area 4 of FIG. 3.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of an adjustable immobilizing joint brace in accordance with the present invention, and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings in detail, wherein like reference numerals indicate like elements throughout, there is shown in FIGS. 1-5, an embodiment of an adjustable immobilizing joint brace ("brace"), generally designated 10, in accordance with the present invention. Though the brace 10 may be used to immobilize an elbow joint (not shown), the brace 10 may also be used to immobilize other joints such as a knee.

Referring to FIG. 1, the brace 10 includes a pair of parallel and spaced apart first supports 12 and a pair of parallel and spaced apart second supports 14. The first and second supports 12, 14 each may include a thin, rectangular bar formed of a rigid and lightweight material such as aluminum. In one example, the first and second supports 12, 14 may be or contain any suitable rigid and/or light weight material such as metal, alloy, steel, a polymeric material, or a composite material and may have any shape so long as the supports 12, 14 can support the brace 10 and immobilize the joint. Similarly, other members of the brace may also be or contain any suitable rigid and/or light weight material such as metal, alloy, steel, a polymeric material, or a composite material.

A first end 12a of each first support 12 is secured to a joint end 14a of a corresponding second support 14 by a pair of first fasteners 16. The first fasteners 16 may be a set of screws such as Allen or Phillip screws. In some examples, the first fasteners 16 may be other known fastener such as a rivet or snap. The use of two first fasteners 16 is may be over one in some applications in order to prevent the first support 12 from moving relative to the second support 14. The first fasteners 16 may be removable such that the first and second supports 12, 14 can be reoriented as further described below. Alternatively, the first supports 12 may be slidably received over or onto the joint end 14a of the second supports 14 and held together by any suitable mechanism, device or means, such as screws, which may hold first supports 12 in position.

Each first and second support 12, 14 is removeably mounted to a first or second pad 18, 20 respectively. The first and second supports 12, 14 may be secured to the first and second pads 18, 20 respectively by second fasteners 22 extending through holes 22a in the first and second supports 12, 14 (FIGS. 2A-5). Though the first and second supports 12, 14 may be moveably mounted to the first and second pads 18, 20, they may also be non-moveably attached to the first and second pads 18, 20. Additionally, though fasteners similar to the first fasteners 16 may be used, the first and second supports 12, 14 may be attached to the first and second pads 18, 20 in any suitable manner such as through the use of an adhesive or by being slid within a receiving slot and/or held by a fastener or a snap fit.

The first and/or second pads 18, 20 may include a lightweight and/or soft cushioning material such as a padded foam material so that the first and/or second pads 18, 20 are comfortable against the skin of a user. The first and second pads 18, 20 may be convex to partially surround and securely fit to the shape of a user's limb. However, the first and second pads 18, 20 may extend further or less far around the outer surface of a user's limb (not shown). The first pad 18 may have a slightly higher radius of convexity than the second pad 20 such that the first pad 18 better conforms to a lower limb such as the forearm or lower leg because of the relative smaller size of the respective forearm and lower leg as compared to the respective upper arm and upper leg. Though the first pad 18 may have a higher radius of convexity and smaller overall size than the second pad 20, the first and convex pads 18, 20 may have a similar shape and size.

A plurality of adjustable straps 24 extends between each pair of the first and second pads 18, 20 respectively. Each of the adjustable straps 24 may be looped around support members 26 provided on the first and second pads 18, 20. Each adjustable strap 24 may loop around the respective support member 26 and overlap back onto itself and is held in place by a hook and loop or Velcro attachment 24a. Though hook and loop or Velcro 24a may be used for securing the adjustable straps 24, other strapping attachments, such as belts, buttons, snaps or elastic material may be utilized.

The first and second pads 18, 20 may have an "I" shaped configuration such that the first and second pads 18, 20 extend at least partially below the adjustable straps 24. The design may prevent the adjustable straps 24 from uncomfortably touching a user's skin. Though the first and second pads 18, 20 may have an "I" shaped configuration to make the brace 10 lighter and more open, they may extend further around the circumference of the limb to further secure the limb, such as a forearm or arm, in position or further stabilize limb support.

Referring now to FIGS. 2A-5, the first supports 12 are oriented with respect to the second supports 14 in such a way as to vary the angle of the brace 10. The first supports 12 may include one of the markings A, B, C, or D on each side of the first support 12 toward the first end 12a or a second end 12b. Markings A and D may be on opposite sides of the first end 12a of the first support 12 and markings B and C may be on opposite sides of the second end 12b of the first support 12. The first support 12 includes a first pair of first joint holes 28 extending through the first end 12a and a second pair of first joint holes 30 extending through the second end 12b. The first and second pairs of first joint holes 28, 30 may be spaced at various positions with respect to the corresponding first or second end 12a, 14a. For example, referring to FIG. 2A, one of the holes of the second pair of first joint holes 30a may be spaced from an edge 12c of the second end 12b by a distance S1 and the other hole of the second pair of first joint holes 30b is spaced from the edge 12c of the second end 12b by a distance S2 where S1 is greater than S2. Though the holes of the first and second pairs of first joint holes 28, 30 may be spaced at various distances from the edge 12c of the first or second end 12a, 12b, respectively, the holes of the first and second pairs of first joint holes 28, 30 may also be spaced at equal distances, or distances other than shown, from the corresponding end 12a, 12b or the that holes (not visible) on the second support 14 may be unequally spaced. Though unequally spaced holes 28, 30 may be used, any other suitable attachment may be used and may be used such that the brace 10 is adjustable as described below.

Figure 5:
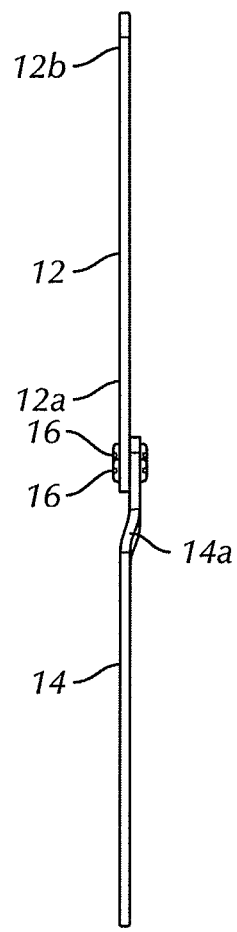
FIG. 5 is a side elevation view of the assembled supports shown in FIG. 2A.
Figure 5A:
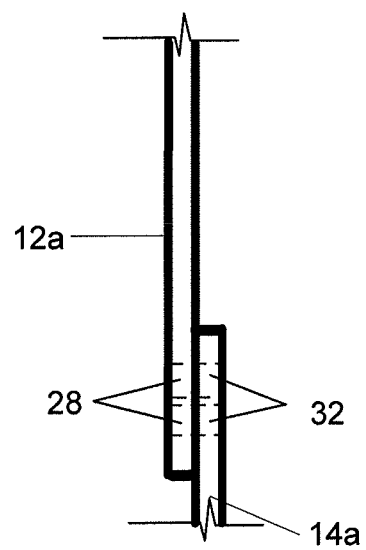
FIG. 5A is an enlarged side elevation view of the first and second supports illustrating respective holes defined therein and aligned with one another in accordance with one embodiment of the present invention.

The first and second pairs of first joint holes 28, 30 are oriented such that positioning the first support 12 onto a joint end 14a via a pair of second joint holes 32 of the second support 14 (shown in FIG. 5A) varies the angle α between the first support 12 and the second support 14. The marking A-D closest to the joint end 14a corresponds to a different angle α between the first support 12 and the second support 14. For example, when the first end 12a of the first support 12 is secured to the second support 14 such that the marking A is facing away from the joint end 14a, the first support 12 may be angled from the second support 14 at a first angle α' corresponding to approximately 30 degrees. When the second end 12b of first support 12 is secured to the second support 14 such that the marking B is facing away from the joint end 14a, the first support 12 is angled from the second support 14 at a second angle α" which corresponds to an angle of approximately 23 degrees. When the second end 12b of the first support 12 is secured to the second support 14 such that the marking C is facing away from the joint end 14a, the first support 12 is angled from the second support 14 at a third angle α''' generally equal to approximately 17 degrees. When the first end 12a of the support 12 is secured to the second support 14 such that the marking D is facing away from the joint end 14a, the first support 12 is angled from the second support 14 at a fourth angle α'''' generally relating to an angle of approximately 10 degrees. Though the above angles α', α", α''' and α'''' may correspond generally to the given values, the angles α', α", α'" and α"" may also correspond to any desired angle. The markings A-D not only help to indicate the appropriate angle α, but also help to ensure that both first supports 12 are attached to the respective second supports 14 in the same position. Though markings A-D may be used to identify the position of the first support 12, any other marking such as numbers, colors or the shape of the end be used.

The joint end 14a of the second support 14 may be stepped outwardly away from the brace 10 such that the first support 12 and second support 14 are generally positioned on the same plane when assembled. Additionally, the joint end 14a of the second support 14 may be angled toward the angle α. In one example, the joint end 14a may be generally flat and straight. And first and second pairs of first joint holes 28, 30 may be used in the first support 12 to vary the angle α between the first support 12 and a second support 14. In some example, additional joint holes (not shown) may be included on either the first or second supports 12, 14 to enable additional combinations between the orientation of the first and second supports 12, 14. Additionally, though the first support 12 may have four configurations as shown and described, it may have more or fewer possible orientations.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. An adjustable immobilizing joint brace comprising:
   a pair of opposed, spaced apart first supports, each of the pair of first supports having a first side and a second side opposite the respective first side and having a pair of first joint holes defined through the respective first and second sides and proximate a first end of a respective one of the pair of first supports, one first joint hole of each pair of first joint holes being spaced farther from the respective first end than the other first joint hole of the respective pair of first joint holes; and
   a pair of opposed, spaced apart second supports, each of the pair of second supports having a first side and a second side opposite the respective first side and having a pair of second joint holes defined through the respective first and second sides and proximate a joint end of a respective one of the pair of second supports, each second joint hole of each pair of second joint holes being configured to be aligned with a corresponding first joint hole of a corresponding pair of first joint holes such that a pair of respective fasteners is receivable through an aligned pair of first and second joint holes to directly attach each first support to a corresponding second support,
   wherein the joint brace is changeable between a first configuration, in which each second support is attachable to a corresponding first support so that the first side of each first support is in contact with the first side of the corresponding second support and forms a first angle between the pair of first supports and the pair of second supports and a second configuration, in which each second support is attachable to the corresponding first support so that the second side of each first support is in contact with the first side of the corresponding second support so as to form a second angle between the pair of first supports and the pair of second supports; and
   wherein the first angle and the second angle differ.

2. The adjustable immobilizing joint brace of claim 1, wherein each first support of the pair of first supports and each second support of the pair of second supports are mounted to first and second pads, respectively.

3. The adjustable immobilizing joint brace of claim 2, wherein at least one of the first and second pads is convexly shaped.

4. The adjustable immobilizing joint brace of claim 3, wherein each of the first and second pads is convexly shaped, and wherein the first pads have a higher radius of convexity than the second pads.

5. The adjustable immobilizing joint brace of claim 2, further comprising
   a first pair of adjustable straps extending between the first pads such that the first pads are secured to opposing sides of a limb on one side of a joint; and
   a second pair of adjustable straps extending between the second pads such that the second pads are secured to opposing sides of the limb on an opposite side of the joint.

6. The adjustable immobilizing joint brace of claim 5, wherein the first pair of adjustable straps and the second pair of adjustable straps are held in place by hook and loop attachments.

7. The adjustable immobilizing joint brace of claim 2, wherein at least one first support of the pair of first supports or one second support of the pair of second supports are removably mounted to the first and second pads, respectively.

8. The adjustable immobilizing joint brace of claim 2, wherein at least one of the first and second pads is generally I-shaped.

9. The adjustable immobilizing joint brace of claim 2, wherein at least one of the first and second pads includes a soft cushioning material or a padded foam cushioning material.

10. The adjustable immobilizing joint brace of claim 1, wherein the pair of first joint holes of each of the pair of first supports is a first pair of first joint holes, wherein each of the pair of first supports has a second pair of first joint holes proximate a second end of a respective one of the pair of first supports, and wherein each of the second pair of first joint holes is configured to be aligned with a corresponding pair of second joint holes of a corresponding second support such that a pair of respective fasteners is receivable through an aligned pair of first and second joint holes to directly attach each first support to the corresponding second support.

11. The adjustable immobilizing joint brace of claim 10, wherein each first support of the pair of first supports includes a plurality of markings.

12. The adjustable immobilizing joint brace of claim 11, wherein each of the plurality of markings corresponds to a different angle formed between the pair of first supports and the pair of second supports.

13. The adjustable immobilizing joint brace of claim 10, wherein the joint brace is changeable between any two configurations from among:
   the first configuration, in which each first pair of first joint holes is aligned with a corresponding pair of second joint holes and the first side of each first support is in contact with the first side of the corresponding second support so as to form the first angle between the pair of first supports and the pair of second supports;
   the second configuration, in which each first pair of first joint holes is aligned with the corresponding pair of second joint holes and the second side of each first support is in contact with the first side of the corresponding second support so as to form the second angle between the pair of first supports and the pair of second supports;

a third configuration, in which each second pair of first joint holes is aligned with the corresponding pair of second joint holes and the first side of each first support is in contact with the first side of the corresponding second support so as to form a third angle between the pair of first supports and the pair of second supports; and a fourth configuration, in which each second pair of first joint holes is aligned with the corresponding second joint holes and the second side of each first support is in contact with the first side of the corresponding second support so as to form a fourth angle between the pair of first supports and the pair of second supports, wherein the first angle, the second angle, the third angle, and the fourth angle differ from each other.

14. The adjustable immobilizing joint brace of claim 1, wherein each of the pair of first supports is secured to a corresponding second support by a pair of fasteners.

15. The adjustable immobilizing joint brace of claim 1, wherein at least one first support or second support of the respective pair of first supports and pair of second supports comprises at least one of metal, alloy, a polymeric material, or a composite material.

16. The adjustable immobilizing joint brace of claim 1, wherein the joint end of each second support of the pair of second supports is stepped.

17. The adjustable immobilizing joint brace of claim 1, wherein the joint end of each second support of the pair of second supports is angled.

18. The adjustable immobilizing joint brace of claim 1, wherein the pair of first supports is generally immovable with respect to the corresponding pair of second supports when the pair of first supports is attached to the corresponding pair of second supports.

* * * * *